United States Patent [19]

Higuchi et al.

[11] 3,962,447

[45] June 8, 1976

[54] NOVEL PRO-DRUG DERIVATIVES OF PYRIDINIUM ALDOXIME TYPE CHOLINESTERASE REACTIVATORS AND METHOD OF USING SAME

[75] Inventors: Takeru Higuchi; Nicolae S. Bodor; Efraim Shek, all of Lawrence, Kans.

[73] Assignee: Interx Research Corporation, Lawrence, Kans.

[22] Filed: Aug. 11, 1975

[21] Appl. No.: 603,612

Related U.S. Application Data

[62] Division of Ser. No. 428,215, Dec. 26, 1973, Pat. No. 3,929,813.

[52] U.S. Cl. .............................................. 424/263
[51] Int. Cl.² ......................................... A61K 31/44
[58] Field of Search............................ 424/263, 267

Primary Examiner—Stanley J. Friedman
Attorney, Agent, or Firm—Charles N. Blitzer

[57] ABSTRACT

There is provided, novel pro-drug forms of pyridinium aldoxime type cholinesterase reactivators, namely, dihydropyridinium aldoximes, having the formula:

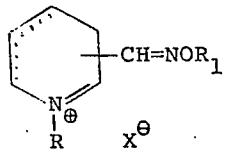

wherein R represents a member selected from the group consisting of an alkyl (C₁-C₄) group, a

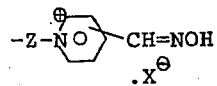

group, a

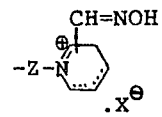

group,

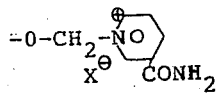

group, and a

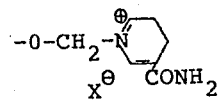

wherein Z represents a member selected from the group consisting of a —CH₂—CH₂— group, a —CH₂—O—CH₂— group, a —CH₂CH₂OCH₂CH₂— group, and a —CH₂O—CH₂—CH₂—O—CH₂— group; wherein R₁ represents a member selected from the group consisting of a hydrogen atom, a methyl group, an acyl group and a

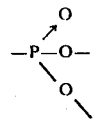

group; and wherein X⁻ represents an anion derived from a pharmaceutically acceptable acid addition salt.

These compounds are useful in reactivating cholinesterase, inhibited following exposure to and/or ingestion of conventional anti-cholinesterase agents, especially in the brain.

32 Claims, No Drawings

NOVEL PRO-DRUG DERIVATIVES OF PYRIDINIUM ALDOXIME TYPE CHOLINESTERASE REACTIVATORS AND METHOD OF USING SAME

This is a division of application Ser. No. 428,215, filed Dec. 26, 1973, now U.S. Pat. No. 3,929,813.

BACKGROUND OF THE INVENTION

1. Field Of The Invention

The present invention is directed to novel pro-drug forms of cholinesterase reactivators, and more specifically, the present invention is directed to pro-drug forms of pyridinium aldoxime type cholinesterase reactivators. A most representative member of this class of cholinesterase reactivators is 1-methyl-pyridinium-2-aldoxime iodide (or chloride or methanesulfonate), hereinafter referred to as "2-PAM."

As employed in this application, the term "pro-drug" refers to a derivatized form of a proven drug, for example, 2 PAM, which when administered to an individual, is enzymatically oxidized in the bloodstream, to the extent that the proven drug (2-PAM) is released at its therapeutic site or sites of activity and especially the brain.

2. Description Of The Prior Art

2-PAM, chemically known as 1-methyl pyridinium-2-aldoxime is a white crystalline, water-soluble powder, usually employed in the chloride form, having the following formula:

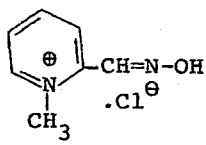

Conventionally, the compound is employed in the form of its acid addition salt, such as, the chloride salt, the iodide salt, or the methanesulfonate salt.

Intoxication by anti-cholinesterase compounds may occur following accidental exposure to organophosphorus insecticides and other toxic chemical agents or even after administration of excessive amounts of drugs like neostigmine, normally employed for the management of glaucoma or myasthenia gravis. The pharmacologic effect of anti-cholinesterases is chiefly due to the inhibition of cholinesterase enzymes throughout the body. The search for satisfactory antidotes to counteract the effect of such toxic agents has led to a series of oxime derivatives of which 2-PAM appears to be the compound of choice, namely because of its physiologic compatibility, its excellent water solubility and its high oxime content per mole of compound. The most striking characteristic of the oxime is that it reactivates cholinesterase, which becomes inhibited by the anti-cholinesterase agent.

The pharmacologic effects of anti-cholinesterases, such as nerve agents (GB and VX), organophosphorus insecticides (Parathion), and quaternary ammonium compounds (neostigmine), may be ascribed to the inhibition of cholinesterase enzymes in the tissues, thereby resulting in cholinergic effects caused by the accumulation of acetylcholine in the effector organs. The chief actions of these compounds can be classified as follows:

1. Muscarine-like effect, manifested by nausea, vomiting, abdominal cramps, diarrhea, sweating, increased salivation, bronchial secretion, and bradycardia;
2. Effect on the central nervous system, characterized by anxiety, headache, and sometimes ataxia, coma, and convulsions; and
3. Nicotine-like effects, including as the most important one, muscular paralysis.

Severe poisoning by anti-cholinesterases results in paralysis of respiration by both central and peripheral effects, with consequent death unless prompt therapy is instituted.

While large doses of atropine abolish the muscarine-like effect, and partially alleviate the central nervous system manifestations of intoxication by the anti-cholinesterase compounds, the peripheral neuromuscular blockade (nicotine-like effect) is not appreciably diminished. See, R. V. Brown, et al., *J. Pharmacol. Exp. Therap.*, 120, 276, (1957); D. Grob, *Arch. Internal Med.*, 98, 221, (1956); and H. M. Kunkel, et al., *Proc. Soc. Exp. Biol. Med.*, 92, 529, (1956).

The neuromuscular blockade, attributable to the accumulation of acetylcholine at the motorend-plate, persists until partial restoration of cholinesterase activity of the muscle can be brought about. The effectiveness of oximes in treating anti-cholinesterase intoxication is attributable largely to their ability to overcome the neuromuscular blockade. The reversal of the neuromuscular blockade produced by alkyl phosphates is believed to be due to reactivation of muscle cholinesterase. See, D. Grob, and R. J. Johns, *Am. J. Med.*, 24, 497, (1958).

Many workers have demonstrated that cholinesterase inactivated by organophosphorus compounds may be reactivated in vitro by oximes. In studies with experimental animals, the actions of anti-cholinesterase agents on smooth, cardiac and skeletal muscles could be reversed by oximes, and in addition, their lethal effects reduced, although the effectiveness of the oximes will vary considerably in different species. See, B. M. Askew, *Brit. J. Pharmacol.*, 11, 417, (1956); R. V. Brown, *J. Pharmacol. Exp. Therap.*, 120, 276, (1957); R. Holmes, and E. L. Robins, *Brit. J. Pharmacol.*, 10, 490, (1955); H. Kewitz, et al., *Arch. Biochem. Biophys.*, 64, 456, (1956); and J. H. Wills, et al., *Science*, 125, 743, (1957).

In man, the intravenous dose of 2-PAM (as the iodide) required to alleviate the toxic effect of a nerve agent, such as G.B. (Sarin) has been reported to be in the range of 14 to 28 mg./Kg. of body weight. See, D. Grob, and R. J. Johns, *Am. J. Med.*, 24, 497, (1958). Consequently, since 1.4 g. of the iodide are equivalent in oxime content to 1 g. of the chloride, the corresponding intravenous dose of 2-PAM chloride is 10 to 20 mg./Kg. of body weight. See, A. A. Kondritzer, et al., *J. Pharm. Sci.*, 50, 109, (1961).

Zvirblis has studied the distribution of 2-PAM in serum and tissues of rabbits. The greatest concentration of 2-PAM was found in the kidney. In man, 2-PAM is eliminated primarily via the kidney. See, P. Zvirblis, unpublished data, U.S. Army Chemical Research and Development Laboratories. Following an intravenous dose of 15 mg. of 2-PAM per Kg. of body weight, the half-life in man has been found to be about 0.8 hours. See, B. V. Jager, and G. N. Stagg, Bull. Johns Hopkins Hosp., 102, 203, (1958). Approximately 80% of the compound was excreted during the first six hours, and most of the unchanged oxime was found in the urine within the first thirty minutes. 2-PAM was not found to be bound appreciably to human serum protein, nor for that matter, to enter the erythrocytes.

Because 2-PAM is an ionic compound (quaternary ammonium salt), it is not expected to cross the blood-brain barrier, although there is conflicting evidence regarding this question. But the most recent evidence indicates that some crossing of the blood-brain barrier does occur in the rat within ten minutes after administration of 2-PAM. Moreover, in patients intoxicated by Parathion, 2-PAM effected rapid recovery of consciousness. See, A. J. Funckes, *Arch. Env. Health*, 1, 104, (1960); T. Nanba, and K. Hiraki, *J. Am. Med. Assoc.*, 166, 1834, (1958); and A. Schuchter, et al., *Arzneimittel Forschg*, 10, 399, (1960). The oxime was found to have significant anti-convulsant action in some patients, this finding supporting the view that oximes do cross the blood-brain barrier.

However, even with such encouraging results, it is well felt among those individuals familiar with 2-PAM that if the same does, in fact, cross the blood-brain barrier, the amount which crosses the barrier is extremely small. Thus, an I.P. (intraperatoneal) dose of 100 mg./Kg. of 2-PAM reactivated only 4% of the cholinesterase in the brain of the rat after intoxication in vivo by Sarin. See, J. P. Rutland, *Brit. J. Pharmacol.*, 13, 399, (1958).

It is speculated that since some body tissues exhibit a pH as high as 8.5 (the pKa of the oxime part of 2-PAM) such a high pH would permit some 2-PAM to dissociate and pass through the blood-brain barrier as a zwitter ion

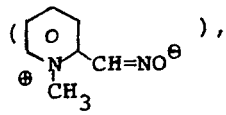

but only in a small amount which would not achieve therapeusis. Experiments also show that 2-PAM does not penetrate all areas of the brain to the same extent, but the test animals are still protected from the lethal effects of paraoxon. See, F. Hobbiger, and V. Vojvodic, *Biochem. Pharmacol.*, 16, 455, (1967).

Furthermore, more recent publications disclose that if a therapeutic amount of 2-PAM fails to reach the brain site immediately, the bound cholinesterase cannot be subsequently regenerated by oximes, i.e., its regeneration is irreversible. This process, called "aging," occurs at different rates, mainly depending on the nature of the poison, i.e., organophosphorus compound. See, E. Heilbronn, *Svensk kemisk tidskr.*, 77, 11, (1965). For example, cholinesterase inhibited by DFP (diisopropyl phosphorofluoridate) is transformed into the non-reactivatable form in a few hours, while aging of a soman inhibited enzyme occurs in 2 minutes. See, W. D. Erdmann, *Naunyn-Schmiedebergs Arch. Pharmak.*, 263, 61, (1969).

As to oral administration of 2-PAM, while the same can be and has been administered orally, the amount of absorption of 2-PAM into the bloodstream amounts to only some 20 to 30 percent. Consequently, the oral route of administering 2-PAM (5 g. initially), in time of need, is less desirable than any of the conventional parenteral approaches, i.e., intravenous, intraperitoneally, or intramuscularly, except for prophylactic use or maintenance in certain intoxications, for example, Parathion. See, H. Edery and G. Schatzberg - Porath, *Arch. Int. Pharmacodyn.*, 121, 104, (1959); A. A. Kondritzer, P. Zvirblis, A. Goodman, and S. H. Paplamus, *J. Pharm. Sci.*, 57, 1142, (1968); F. R. Sidell, N. A. Groff, and R. J. Ellin, ibid, 58, 1093, (1969); F. R. Sidell and N. A. Groff, ibid, 60, 860, (1971); F. R. Sidell, N. A. Groff, and A. Kaminskis, ibid, 61, 1136, (1972); respectively.

In summary then, 2-PAM, while useful to some extent in overcoming the effects of anti-cholinesterase agents, still leaves much to be desired in terms of (1) its inability to appreciably pass through the blood-brain barrier, (2) its extremely poor bioavailability, and (3) its unfavorable distribution, poor retention rate in the body, and/or no protein binding.

SUMMARY OF THE INVENTION

Accordingly, it is one object of the present invention to provide novel pro-drug forms of 2-PAM and related pyridinium aldoximes, which when placed in the bloodstream of a warm-blooded animal exists in a non-ionic form so as to also permit passage of same through the blood-brain barrier, after which, the compound is enzymatically oxidized to release 2-PAM or the corresponding pyridinium aldoxime at its therapeutic site or sites of activity.

It is a second object of the present invention to provide novel compounds as described above which when administered orally to a warm-blooded animal, will be absorbed through the intestinal tract and introduced into the bloodstream at high bio-availability levels, after which enzymatic oxidation will occur to release 2-PAM or a corresponding pyridinium aldoxime at its therapeutic site or sites of activity.

Finally, it is a third object of the present invention to provide novel compounds as described above, which when placed in the bloodstream of a warm-blooded animal, via any route of administration, will pass through the blood-brain barrier, be enzymatically oxidized to 2-PAM or to the corresponding pyridinium aldoxime, thus permitting the same to act therapeutically at all body sites of need, including the brain, and yet, be retained by the body in such a manner as to be eliminated at a rate commensurate with therapeusis. That is, substantial protein binding will occur, before its transformation into 2-PAM or the corresponding pyridinium aldoxime.

Accordingly, all of the foregoing objects are achieved by administering to a warm-blooded animal, e.g., a mammalian species, by any suitable route of administration (orally, intravenously, intramuscularly, or intraperitoneally), a compound of the formula:

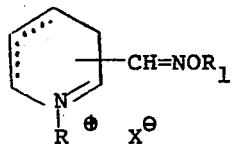

wherein R represents a member selected from the group consisting of an alkyl ($C_1$-$C_4$) group, a

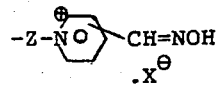

group, a group,

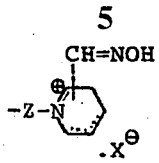

group, and a

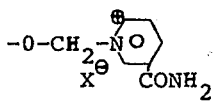

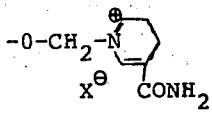

wherein Z represents a member selected from the group consisting of a —CH$_2$—CH$_2$— group, a —CH$_2$—O—CH$_2$— group, a —CH$_2$CH$_2$OCH$_2$CH$_2$— group, and a —CH$_2$O—CH$_2$—CH$_2$—O—CH$_2$— group; wherein R$_1$ represents a member selected from the group consisting of a hydrogen atom, a methyl group, an acyl group and a

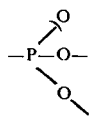

group; and wherein X$^-$ represents an anion derived from a pharmaceutically acceptable acid addition salt.

These compounds are useful in reactivating cholinesterase, inhibited following exposure to and/or ingestion of conventional anti-cholinesterase agents, especially in the brain.

With reference to the generic formula for the pro-2-PAM and related pyridinium aldoxime compounds of this invention, X represents an anion derived from a pharmaceutically acceptable acid addition salt. The phrase "pharmaceutically acceptable acid addition salt" as used herein, refers to non-toxic pharmaceutically acceptable acid addition salts formed from non-toxic inorganic or organic acids. For example, but without limitation, the salts include those derived from inorganic acids such as hydrochloric, hydrobromic, sulfuric, sulfamic, phosphoric, and the like; and the salts prepared from organic acids, such as acetic, propionic, succinic, glycollic, stearic, lactic, malic, tartaric, citric, ascorbic, pamoic, maleic, hydroxymaleic, phenylacetic, glutamic, benzoic, salicylic, sulfanilic, fumaric, toluenesulfonic, and the like.

DETAILED DESCRIPTION OF THE INVENTION

The term "warm-blooded" animal as employed in this application refers to any warm-blooded animal, though the mammalian species is preferred, since it is the species most often affected by anti-cholinesterase agents.

As mentioned earlier, 2-PAM is an ionic species; that is, it is a quaternary salt, and because of this ionic feature, 2-PAM cannot readily pass through the blood-brain barrier. As such, therapeutic levels of 2-PAM in the brain cannot be achieved.

Quite uniquely, the present inventors approached the blood-brain barrier impediment of 2-PAM from a unique standpoint. They first realized that 2-PAM derivatives had to be developed, which (1) would be non-ionic when they reached the bloodstream, and (2) would be subsequently enzymatically oxidized to release 2-PAM in a therapeutic amount at the body's site or sites of need, and especially, the brain. To this end, they developed pro-drug forms of 2-PAM and related compounds which uniquely contain a tertiary nitrogen atom, exhibiting a low basicity, i.e., a pKa below 7.4, and thus a pKa of 6.32 in the case of the pro-2-PAM. On this basis, the skilled artisan can readily appreciate that such compounds, when introduced into the bloodstream of a warm-blooded animal whose pH is about 7.4 would remain essentially non-ionic, thus permitting the pro-drug form to be highly protein bounded and/or enter the erythrocytes and thus to pass through the blood-brain barrier and be subsequently enzymatically oxidized to release 2-PAM or a related pyridinium aldoxime in high bio-availability levels at the body's therapeutic site or sites of need. In this vein, the compounds encompassed by the above-generic formula function in the manner described above. In addition to containing a tertiary nitrogen atom having a pKa of about 6.32, and thus, essentially, non-protonated at the pH of plasma, the observer will readily appreciate the fact that the compounds of this invention are not quaternary salts. As such, they readily pass the blood-brain barrier.

With respect to the salt feature (acid addition salt) of the compounds of this invention, the salt form is employed for the sole purpose of rendering stability to the pro-drug free base form, prior to administration. That is, once the pro-drug compounds of this invention are administered by any route, the salt moiety is "cleaved," thus releasing the remaining tertiary amine form, which readily transcends the blood-brain barrier. Next, the pro-drug is oxidized enzymatically to 2-PAM or the related pyridinium aldoxime in an analogous manner to the nicotinamide dinucleotide (NAD) co-enzyme mediated oxido-reduction system; where the coenzyme, in turn, is reduced to the dihydro form (NADH). For details about this enzymatic oxido-reductive system see, U. Eisner and J. Kuthan, "The Chemistry of Dihydropyridines," *Chem. Rev.*, 72, 1 (1972).

It should be emphasized that in one instance, a pro-drug form of this invention will release 2-PAM in the bloodstream following enzymatic oxidation. In the other instances, related pyridine aldoxime derivatives will be released. In any event, the ultimate pyridine aldoxime compound released (other than 2-PAM) will function in the same manner as 2-PAM to reactivate bound cholinesterase.

While all the compounds of this invention will achieve the objectives previously outlined, certain compounds are preferred as follows:

1. 1-methyl-1,6-dihydropyridine-2-aldoxime and its HX salts, wherein X represents a pharmaceutically acceptable anion.
2. Trimethylene-bis-[1-(1,6- or 1,4-dihydropyridine-4-aldoxime] and its di-HX salts, wherein X represents a pharmaceutically acceptable anion.
3. Bis-(4-hydroxyiminomethyl-1,6- or -1,4-dihydropyridine-1-methyl) ether and its HX salts, wherein X represents a pharmaceutically acceptable anion.

4. Bis-(2-hydroxyiminomethyl-1,6-dihydropyridine-1-methyl) ether and its HX salts, wherein X represents a pharmaceutically acceptable anion.
5. Bis-[2-(4-hydroxyiminomethyl-1,6- or 1,4-dihydropyridino) ethyl] ether and its HX salts, wherein X represents a pharmaceutically acceptable anion.

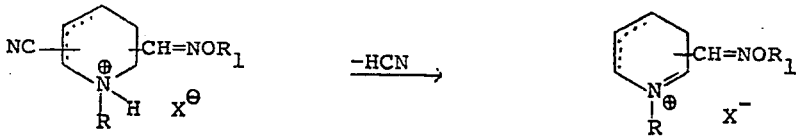

6. Ethylene glycol bis-(4-hydroxyimino-methyl-1,6 or 1,4-dihydropyridine-1-methyl) ether and its HX salts, wherein X represents a pharmaceutically acceptable anion.

The anion defined by X is obtained from any pharmaceutically acceptable acid addition salt as defined earlier.

The compounds of this invention can be prepared according to the following reaction scheme:

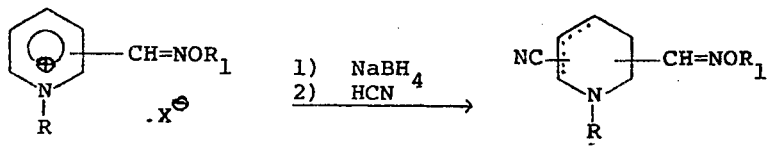

The first two steps are carried out at standard temperature (preferably at 20° – 25°C.) and standard pressure in an $N_2$ atmosphere, using a reducing agent, such as any metal hydride, sodium dithionite, but preferably sodium borohydride ($NaBH_4$), and a good nucleophile, preferably HCN (formed from NaCN and HCl) in a homogeneous solvent system (e.g., water, water-alcohol, water-tetrahydrofuran, etc.) or a heterogenous solvent system (e.g., water-ethyl ether, water-benzene, water-toluene, etc.: 3/10 vol./vol.) for about 5 hours with vigorous stirring. The tetrahydro derivative is either the 1,2,3,6, or the 1,2 3,4, depending on the position of the oxime type group, and is crystallized from a suitable solvent, preferably from ether.
(Step 3)

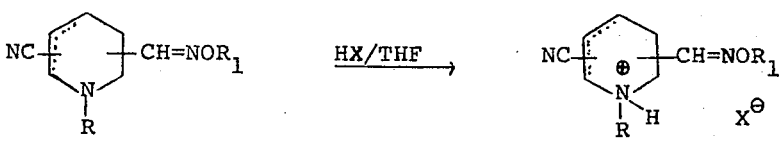

furan (THF) saturated with anhydrous HX (X is defined as set forth earlier, but preferably Cl). The salt formed is collected by filtration, after stirring the mixture for about one-half hour and cooling.
(Step 4)

In the last step, elimination of HCN is carried out at standard temperature and pressure, under a standard $N_2$ atmosphere, in a $C_1$-$C_3$ aliphatic alcoholic solvent, methanol being preferred, for several hours (preferably 1 to 2 hours). During the reaction, the starting material is dissolved and a new product, the final dihydropyridinium salt is precipitated. Depending on the position of the oxime and of the CN groups in the starting material, the salt of a 1,6- or 1,4-dihydropyridine derivative is obtained.

As all the salts exist in an enamine form, the double bond(s) of the obtained dihydropyridine ring will rearrange during the salt formation, i.e., during the elimination process. Thus, the following basic enamine - salt types (isomers) are possible:

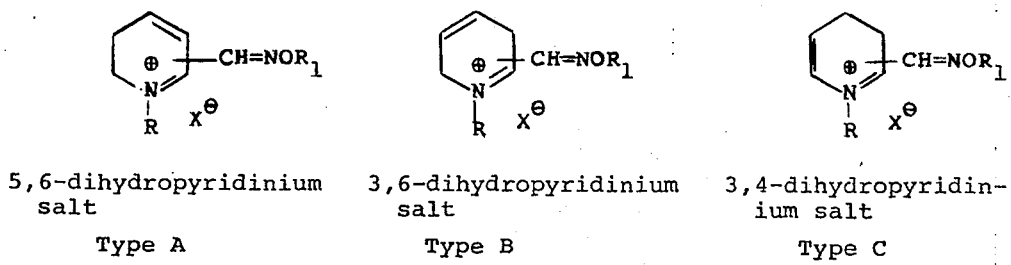

5,6-dihydropyridinium salt    3,6-dihydropyridinium salt    3,4-dihydropyridinium salt
Type A                        Type B                        Type C It is well known that the relative energy difference between dihydropyridine isomers is small (less than 4 Kcal/mole). Thus, they can usually rearrange into another, on the simple action of a solvent.

For any skilled artisan it will be obvious that the position of the double bonds in the above types is controlled both kinetically and thermodynamically. However, from the point of view of the present invention, i.e., the ease to be oxidized, back to a pyridinium ring, the question as to which isomer will be obtained, is absolutely irrelevant. All three possible isomers have the same value from the view of the present invention, and they are all considered as part of the basic idea of this invention.

All steps of the synthesis are carried out under vigorous non-oxidizing conditions in order to prevent premature oxidation of the dihydropyridine derivatives into pyridinium form. In step (1), an equimolar ratio of reactants can be employed. In step (2), an equimolar ratio of reactants can be employed, though an excess of HCN is preferred. In step (3), an equimolar ratio of reactants can be employed, though an excess of HX is preferred.

The uniqueness of the process employed to prepare the compounds of this invention resides in the fact that first, the reduction step is stopped after reduction of only one double bond (addition of two hydrogen atoms) of the pyridine ring, by addition of a suitably good nucleophile leaving group (HCN, HSCN, etc.) on one of the double bonds of the dihydropyridine derivative formed. Otherwise, reduction could not be stopped at the dihydro stage and various tetrahydro derivatives would form which cannot be transformed back to the necessary dihydro derivatives. (It is known that tetrahydropyridinium oximes are inactive as cholinesterase reactivators).

Secondly, the cyano adduct formed is a relatively stable intermediate which can be well stabilized in its protonated salt form, which, on the other hand can be transformed easily into the desired dihydropyridinium salt, by elimination of an HCN molecule, using the conditions described earlier.

These compounds can be administered parenterally (I.V., I.P., or I.M.) by simply combining a therapeutic effective amount of same with any pharmaceutically acceptable inert parenteral carrier, and with respect to oral administration, since the compounds of the present invention are absorbed effectively through the intestine, and on the other hand, being highly sensitive compounds, they must be administered in a therapeutic amount by means of an inert enteric coated medium. With respect to either dosage form, parenteral or oral, it should be emphasized that the carrier material, in either case, must be inert (non-oxidizing) in nature. The reason for this, is that if the compounds of this invention are contacted with an oxidizing agent prior to entrance into the bloodstream, the compound will be oxidized to 2-PAM or the like aldoxime compound immediately, and as such, the purpose and objectives of the present invention would be defeated. While detailed examples will be provided later in the application, demonstrating the preparation and administration of a parenteral and oral dosage form suitable for this invention, the ordinary skilled artisan can readily acquaint himself with such forms by referring to the text entitled REMINGTON'S PHARMACEUTICAL SCIENCES, Fourteenth Edition (1970), pgs. 1519–1544 and 1689–1691, respectively.

A better understanding of the present invention will be gained from the following examples, which are simply intended to be illustrative and non-limitative of the present invention.

EXAMPLE I (Preparation of 1-methyl-1,6-dihydropyridine-2-aldoxime hydrochloride)

Firstly, the precursor compound, 1-methyl-2-cyano-1,2,3,6-tetrahydropyridine-2-aldoxime was prepared.

To a solution of 76 g. (1.55 mol) of sodium cyanide in 300 ml. of freshly distilled water, saturated with nitrogen, there was added 114 ml. of 18% hydrochloric acid. The aqueous solution was layered with 1000 ml. of distilled ether and cooled to 15° C. One hundred (100) g. (0.38 mol) of 2-pyridine aldoxime methiodide (2-PAM) was added to the cold solution. Subsequently, 19 g. (0.495 mol) of sodium borohydride ($NaBH_4$) was added and the solution was warmed to 25° C and kept at that temperature for 5 hours with vigorous stirring. The ether layer was separated and the water layer was filtered, the precipitate being extracted with ether. The combined ether layers were evaporated. The precursor compound was purified by washing with 30% diethyl ether in cyclohexane. The yield of the precursor compound was 44.5 g. (71%), and the melting point of same was 112°–115° C (decomp). The NMR spectrum was consistent with the structure of the compound obtained. Analysis calculated for $C_8H_{11}ON_3$: C, 58.15; H, 6.67; and N, 25.45. Found: C, 58.34; H, 7.01; and N, 25.22. IR. spectra: Weak, 1630 $cm^{-1}$, 1665 $cm^{-1}$: C=C, C=N; Strong: 955 $cm^{-1}$: N—O; 2740 $cm^{-1}$, 1445 $cm^{-1}$: N—$CH_3$; 3180 $cm^{-1}$: O—H.

Subsequently, 200 ml. of tetrahydrofuran (peroxide free) was saturated with hydrogen chloride gas. Fifteen (15) g. of the precursor compound was added and the mixture was stirred for 30 minutes. The mixture was then cooled and the precipitate was collected, washed with ether, and dried in vacuo. In this manner, the hydrochloride form of the precursor compound was obtained in a yield of 17.5 g. (95%), mp 127°–130° C (decomp). Analysis calulated for $C_8H_{12}ON_3Cl$: C, 47.64; H, 5.96; N, 20.84. Found: C, 47.39; H, 5.93; N, 20.57. IR. spectra: (KRr pellet) >$N^+$-H at 2260 $cm^{-1}$ (broad); Weak: 1640, 1675 $cm^{-1}$: C=C, C=N; Strong: 970 $cm^{-1}$: N—O; 3180 $cm^{-1}$: O—H.

To 200 ml. of cooled, but freshly boiled methanol, 17.0 g. (0.084 mol) of the hydrochloride form of the precursor compound (1-methyl-2-cyano-1,2,3,6-tetrahydropyridine hydrochloride) obtained earlier was added. The suspension was mixed under nitrogen for 1½ hours. During that time, a solution was formed and a new product was precipitated. The product was filtered, washed with ether, and dried in vacuo to yield 11.7 g. (80%) of the objective compound (1-methyl-1,6-dihydropyridine-2-aldoxime hydrochloride), mp 179° C (decomp). The NMR spectrum was consistent with the structure of the compound obtained. The analysis of the compound by I.R. (KBr pellet) showed strong and medium bands at 1655, 1700. U.V. analysis in 0.1 N HCl-251 nm ($\epsilon$=13,300); pH of 8 - 308 nm; 0.1N NaOH-260 nm ($\epsilon$=7640) and 340 nm ($\epsilon$=5440).

Analysis calculated for $C_7H_{11}N_2OCl$: C, 48.14; H, 6.30; and N, 16.04. Found: C, 47.86; H, 6.59; and N, 15.97.

By following the procedure outlined above for Example I and using the appropriate reactants, the remaining compounds of the present invention can easily be obtained.

The pKa of the tertiary amine was determined to be 6.32 ± 0.06 by titration and U.V. methods. The pKa of the oxime moiety is about 10.5 as determined by the U.V. noted above.

EXAMPLE II

IN VIVO CHOLINESTERASE REACTIVATION STUDIES 1-methyl-1,6-dihydropyridine-2-aldoxime hydrochloride (the compound of Example I), noted as DPAM was evaluated for its ability to protect against anti-cholinesterase agent toxicity, commensurate with the prescribed procedure set forth by R. A. Lehman and M. E. Nicholas, *Proc. Soc. Expt. Biol. Med.*, 104, 550 (1960). Specifically, an anti-cholinesterase agent, phospholine iodide was injected I.P. (intraperitoneally) at twice the lethal dose into white mice of male sex, weighing about 30.0 plus or minus 3.0 g. Four groups of ten mice each were studied as outlined below in Table I. When using 2-PAM, the same is injected I.P. immediately following phospholine iodide administration. However, when 1-methyl-1,6-dihydropyridine-2-aldoxime hydrochloride was employed, the same was injected ten minutes after the mice were dosed with phospholine iodide.

TABLE I

| GROUP | 2-PAM-Cl 10 mg./cc. | DPAM-HCl 10 mg./cc. | PHOSPHOLINE IODIDE 0.1 mg./cc. | SALINE | SURVIVED |
|---|---|---|---|---|---|
| I | — | — | 0.5 mg./kg. (twice the LD$_{50}$) | 0.2 cc | 1/10 |
| II | 50 mg./Kg. | — | 0.5 mg./Kg. (twice the LD$_{50}$) | — | 10/10 |
| III | — | 50 mg./Kg. | 0.5 mg./Kg. (twice the LD$_{50}$) | — | 10/10 |
| IV | — | 50 mg./Kg. | — | 0.2 cc | 10/10 |

EXAMPLE III (2-PAM CHLORIDE AND 1-METHYL-1,6-DIHYDROPYRIDINE-2-ALDOXIME-HYDROCHLORIDE CONCENTRATIONS IN BLOOD AFTER I.V. ADMINISTRATION)

In accordance with the procedure outlined by J. R. May, P. Zvirblis, and A. A. Kondritzer, *J. Pharm. Sci.*, 54, 1508 (1965), Beagle dogs were injected intravenously with the above-identified compounds for the purpose of determining their concentrations, respectively, in the blood. The Beagle dogs employed were of both sexes and weighed approximately 15.0 Kg. The results obtained are set forth in Table II below:

TABLE II

| | 2-PAM-Cl 5 mg./Kg. | | DPAM-Cl 5 mg./Kg. | |
|---|---|---|---|---|
| TIME (MINUTES) | mcg./ml. plasma | mcg./ml. whole blood | mcg./ml.* plasma | mcg./ml.* whole blood |
| 5 | 11.45 | 5.73 | 4.40 | 6.60 |
| 10 | 11.00 | 5.50 | 3.70 | 4.80 |
| 15 | 5.68 | 2.84 | 3.03 | 4.70 |
| 30 | 5.55 | 2.78 | 1.46 | 4.50 |
| 45 | 2.45 | 1.23 | 2.08 | 4.27 |
| 60 | 1.25 | — | 1.65 | 3.90 |
| 120 | .80 | — | — | 2.75 |
| 180 | — | — | 1.39 | 2.30 |
| 240 | — | — | 0.86 | 1.63 |
| 300 | — | — | — | 1.50 |
| 360 | — | — | — | 0.82 |

*Analyzed as 2-PAM-Cl

In addition to the foregoing study, the excretion (elimination) half-life ($t$ ½) of each compound injected was determined on the basis of the blood studies obtained from Table II above. The half-life values for 2-PAM chloride and 1-methyl-1,6-dihydropyridine-2-aldoxime hydrochloride are set out in Table III below.

TABLE III

| $t$ ½ in Beagle Dogs (5 mg./Kg.) | | Medium |
|---|---|---|
| 2-PAM-Cl | DPAM-Cl | |
| 105 minutes | 168 minutes | Whole Blood |
| | 150 minutes | Plasma |

The importance of the above results shown in Tables II and III respectively, is as follows.

As indicated earlier, 2-PAM, in salt form, is a quaternary pyridinium salt, and it is therefore distributed only in the plasma, practically none of the drug being observed in the blood cells or blood proteins. This is obvious from the data set forth above, since the volume of plasma is approximately one-half of the blood. Therefore, the plasma concentrations of 2-PAM chloride are twice that of the concentration of 2-PAM chloride in the whole blood.

On the other hand, a compound of this invention, 1-methyl-1,6-dihydropyridine-2-aldoxime hydrochloride (DPAM), which is a tertiary amine in the free-base form at the pH of blood (approximately 7.4), is distributed mainly in the blood cells and blood proteins. Consequently, the distribution ratio between the plasma versus whole blood is 1:3. In other words, twice as much of the derivative is in the blood cells and proteins than in the plasma. This assures transport of the pro-2-PAM compound through the blood-brain barrier, whereby through metabolic oxidation (described earlier), 2-PAM or a related pyridinium aldoxime can reach the brain site.

The excretion (elimination) half-life ($t$ ½) is substantially increased in the case of DPAM. This is due to the compound's protein and blood cell binding ability. Moreover, it logically follows that DPAM is oxidized into 2-PAM before it follows the elimination pattern of 2-PAM.

The result of the phenomenon observed with pro-2-PAM is that the therapeutic level of the same does not drop as fast as is the case when employing 2-PAM per se. Consequently, less frequent multiple doses will be necessary for the pyridinium aldoxime compounds of this invention as it can be expected that the $t$ ½ for whole blood is somewhat longer for these compounds. It is theorized that the difference is due to the small time difference observed for the release and oxidation processes.

Urinary analysis at 12, 24 and 48 hours after parenteral administration of the pro-2-PAM compound (1-methyl-1,6-dihydropyridine-2-aldoxime hydrochloride) results in a 70 to 80 percent recovery of the product as 2-PAM in the urine. This proves that the pro-drug form is transferred into 2-PAM without any other significant secondary metabolic pathways.

Existing publications, which concern the elimination study of 2-PAM per se clearly indicate that 90 or more percent of 2-PAM is recovered following administration, which fact clearly points in the direction of nonbody retention. See, B. V. Jager, G. N. Stagg, and L. Jager, *Bull. Johns Hopkins Hosp.*, 102, 225 (1958); F. R. Sidell and W. A. Groff, *J. Pharm. Sci.*, 60, 124 (1971); and F. R. Sidell and A. Kaminskis, *J. Pharm. Sci.*, 61, 1765 (1972), respectively.

Based on the above results, it can be expected that oral administration of the pyridinium aldoxime compounds of this invention will lead to at least 50 or more percent absorption of same as 2-PAM versus 20 to 30 percent when orally administering 2-PAM per se.

As indicated earlier, when administering the pyridinium aldoxime compounds of this invention orally, they must be administered in the form of an enteric coated tablet as it has been determined that oral absorption occurs in the intestine. Therefore, any inert enteric coating can be employed so long as it will protect the pro-2-PAM compound of this invention from dissolution as it passes through the stomach and disintegrates in the small intestine. Normally, the enteric coating material is a cellulose lower fatty acid phthalate, particularly cellulose acetate phthalate. However, other cellulose derivatives can also be employed. For example, cellulose ethers or mixed ether esters can be substituted for the cellulose esters. Thus, among the enteric coating materials which can be used are the materials formed by reacting cellulose acetate, cellulose propionate, cellulose acetate butyrate, ethyl cellulose butylcellulose, etc., with phthalic or maleic anhydrides or the like in the presence of a tertiary organic base. The only limitation on the enteric coating is that it shall preserve the pyridinium aldoxime compounds from dissolution until they reach the small intestine and that the enteric medium be inert (non-oxidizing). Consequently, in addition to the coating enumerated above, one can use any of the conventional enteric coatings, such as shellac and others described in that portion of REMINGTON'S PRACTICE OF PHARMACY, referred to earlier in this application.

In treating the individual poisoned by an anti-cholinesterase blocking agent, therapeusis will be achieved, I.V. by administering about 2.5 g. to the individual initially, and then, administering one-half of that amount (1.25 g.) thereafter at 30 minute intervals until muscle strength is returned; or in the alternative, orally administering the compound of this invention in an initial dosage amount of 5.0 g. followed by the administration of the same in a dosage amount of 2.5 g. at 30 minute intervals until muscle strength return is observed.

Although the present invention has been described in great detail with reference to the specification and examples included therein, it is obviously apparent that various changes and/or modifications can be made to the same by the skilled artisan without departing from the spirit and scope thereof.

Consequently, such changes and modifications are properly, equitably and intended to be within the full range of equivalence of the following claims.

What we claim is:

1. A pharmaceutical composition for reactivating blocked cholinesterase in a warm-blooded animal and suitable for oral administration and absorption through the small intestine of said warm-blooded animal, comprising an effective cholinesterase reactivating amount of a pro-drug compound of the pyridine aldoxime-(hydroxyiminomethyl pyridinium) type capable of reactivating blocked cholinesterase having the formula:

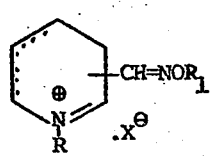

wherein R represents a member selected from the group consisting of an alkyl ($C_1$-$C_4$) group, a

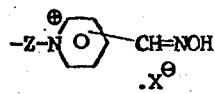

group, a

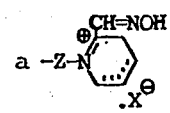

a group,

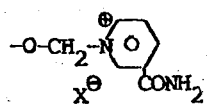

group, and a

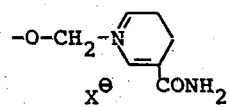

group, wherein Z represents a member selected from the group consisting of a —$CH_2$—$CH_2$— group, a —$CH_2$—O—$CH_2$— group, a —$CH_2CH_2OCH_2CH_2$— group, and a —$CH_2O$—$CH_2$—$CH_2$—O—$CH_2$— group; wherein $R_1$ represents a member selected from the group consisting of a hydrogen atom, a methyl group, an acyl group and a

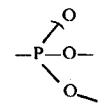

group; and wherein $X^-$ represents an anion derived from a pharmaceutically acceptable acid addition salt in combination with a pharmaceutically acceptable enteric carrier.

2. The composition of claim 1, wherein said compound is: 1-Methyl-1,6-dihydropyridine-2-aldoxime and its HX salts, wherein X represents a pharmaceutically acceptable anion.

3. The composition of claim 1, wherein said compound is: Trimethylene-bis-[1-(dihydropyridine-4-carbaldoxime)] and its di-HX salts, wherein X represents a pharmaceutically acceptable anion.

4. The composition of claim 3, wherein said compound is: Trimethylene-bis-[1-(1,4-dihydropyridine-4-carbaldoxime] and its di-HX salts, wherein X represents a pharmaceutically acceptable anion.

5. The composition of claim 3, wherein said compound is: Trimethylene-bis-[(1,6-dihydropyridine-4-carbaldoxime] and its di-HX salts, wherein X represents a pharmaceutically acceptable anion.

6. The composition of claim 1, wherein said compound is: Bis-(4-hydroxyiminomethyl-dihydropyridine-1-methyl) ether and its di-HX salts, wherein X represents a pharmaceutically acceptable anion.

7. The composition of claim 6, wherein said compound is: Bis-(4-hydroxyiminomethyl-1,4-dihydropyridine-1-methyl) ether and its di-HX salts, wherein X represents a pharmaceutically acceptable anion.

8. The composition of claim 6, wherein said compound is: Bis-(4-hydroxyiminomethyl-1,6-dihydropyridine-1-methyl) ether and its di-HX salts, wherein X represents a pharmaceutically acceptable anion.

9. The composition of claim 1, wherein said compound is: Bis-(2-hydroxyiminomethyl-1,6-dihydropyridine-1-methyl) ether and its di-HX salts, wherein X represents a pharmaceutically acceptable anion.

10. The composition of claim 1, wherein said compound is: Bis-[2-(4-hydroxyiminomethyl-dihydropyridino)ethyl] ether and its di-HX salts, wherein X represents a pharmaceutically acceptable anion.

11. The composition of claim 10, wherein said compound is: Bis-[2-(4-hydroxyiminomethyl-1,4-dihydropyridino) ethyl] ether and its di-HX salts, wherein X represents a pharmaceutically acceptable anion.

12. The composition of claim 10, wherein said compound is: Bis-[2-(4-hydroxyiminomethyl-1,6-dihydropyridino) ethyl] ether and its di-HX salts, wherein X represents a pharmaceutically acceptable anion.

13. The composition of claim 1, wherein said compound is: Ethylene glycol-bis-(4-hydroxyiminomethyl-dihydropyridine-1-methyl) ether and its di-HX salts, wherein X represents a pharmaceutically acceptable anion.

14. The composition of claim 13, wherein said compound is: Ethylene glycol-bis-(4-hydroxyiminomethyl-1,4-dihydropyridine-1-methyl) ether and its di-HX salts, wherein X represents a pharmaceutically acceptable anion.

15. The composition of claim 13, wherein said compound is: Ethylene glycol-bis-(4-hydroxyiminomethyl-1,6-dihydropyridine-1-methyl) ether and its di-HX salts, wherein X represents a pharmaceutically acceptable anion.

16. A method for reactivating blocked cholinesterase in a warm-blooded animal as a result of anticholinesterase compound poisoning, which comprises:
administering thereto, an effective cholinesterase reactivating amount of a pro-drug compound of the pyridine aldoxime (hydroxyiminomethyl pyridinium) type capable of reactivating blocked cholinesterase having the formula:

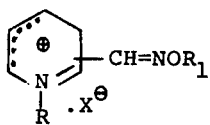

wherein R represents a member selected from the group consisting of an alkyl (C$_1$-C$_4$) group, a

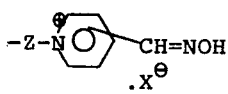

group, a

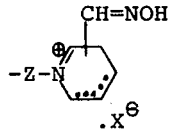

group,

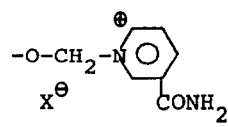

group and a

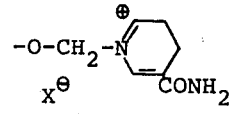

group, wherein Z represents a member selected from the group consisting of a —CH$_2$—CH$_2$— group, a —CH$_2$—O—CH$_2$— group, a —CH$_2$CH$_2$OCH$_2$CH$_2$— group, and a —CH$_2$O—CH$_2$—CH$_2$—O—CH$_2$— group; wherein R$_1$ represents a member selected from the group consisting of a hydrogen atom, a methyl group, an acyl group and a

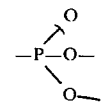

group; and wherein X$^-$ represents an anion derived from a pharmaceutically acceptable acid addition salt.

17. The method of claim 16, wherein said compound is: 1-Methyl-1,6-dihydropyridine-2-aldoxime and its HX salts, wherein X represents a pharmaceutically acceptable anion.

18. The method of claim 16, wherein said compound is: Trimethylene-bis-[1-(dihydropyridine-4-carbaldoxime)] and its di-HX salts, wherein X represents a pharmaceutically acceptable anion.

19. The method of claim 18, wherein said compound is: Trimethylene-bis-[1-(1,4-dihydropyridine-4-carbaldoxime] and its di-HX salts, wherein X represents a pharmaceutically acceptable anion.

20. The method of claim 18, wherein said compound is: Trimethylene-bis-[(1,6-dihydropyridine-4-carbaldoxime] and its di-HX salts, wherein X represents a pharmaceutically acceptable anion.

21. Th method of claim 16, wherein said compound is: Bis-(4-hydroxyiminomethyl-dihydropyridine-1-methyl) ether and its di-HX salts, wherein X represents a pharmaceutically acceptable anion.

22. The method of claim 21, wherein said compound is: Bis-(4-hydroxyiminomethyl-1,4-dihydropyridine-1-methyl) ether and its di-HX salts, wherein X represents a pharmaceutically acceptble anion.

23. The method of claim 21, wherein said compound is: Bis-(4-hydroxyiminomethyl-1,6-dihydropyridine-1-methyl) ether and its di-HX salts, wherein X represents a pharmaceutically acceptable anion.

24. The method of claim 16, wherein said compound is: Bis-(2-hydroxyiminomethyl-1,6-dihydropyridine-1-methyl) ether and its di-HX salts, wherein X represents a pharmaceutically acceptable anion.

25. The method of claim 16, wherein said compound is: Bis-[2-(4-hydroxyiminomethyl-dihydropyridino)

ethyl] ether and its di-HX salts, wherein X represents a pharmaceutically acceptable anion.

26. The method of claim 25, wherein said compound is: Bis-[2-(4-hydroxyiminomethyl-1,4-dihydropyridino) ethyl] ether and its di-HX salts, wherein X represents a pharmaceutically acceptable anion.

27. The method of claim 25, wherein said compound is: Bis-[2-(4-hydroxyiminomethyl-1,6-dihydropyridino) ethyl ] ether and its di-HX salts, wherein X represents a pharmaceutically acceptable anion.

28. The method of claim 16, wherein said compound is: Ethylene glycol-bis-(4-hydroxyiminomethyl-dihydropyridine-1-methyl) ether and its di-HX salts, wherein X represents a pharmaceutically acceptable anion.

29. The method of claim 28, wherein said compound is: Ethylene glycol-bis-(4-hydroxyiminomethyl-1,4-dihydropyridine-1-methyl) ether and its di-HX salts, wherein X represents a pharmaceutically acceptable anion.

30. The method of claim 28, wherein said compound is: Ethylene glycol-bis-(4-hydroxyiminomethyl-1,6-dihydropyridine-1-methyl) ether and its di-HX salts, wherein X represents a pharmaceutically acceptable anion.

31. The method of claim 16, wherein said compound is maintained in combination with a pharmaceutically acceptable enteric carrier.

32. The method of claim 16, wherein said compound is maintained in combination with a pharmaceutically acceptable parenteral vehicle.

* * * * *